(12) United States Patent
Schelges et al.

(10) Patent No.: US 11,554,085 B2
(45) Date of Patent: Jan. 17, 2023

(54) COMBAR FOR SKIN AND HAIR TREATMENT

(71) Applicant: Henkel AG & Co. KGaA, Duesseldorf (DE)

(72) Inventors: Heike Schelges, Willich (DE); Elvira Scholz, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 289 days.

(21) Appl. No.: 16/928,704

(22) Filed: Jul. 14, 2020

(65) Prior Publication Data

US 2021/0015728 A1 Jan. 21, 2021

(30) Foreign Application Priority Data

Jul. 16, 2019 (DE) ..................... 10 2019 210 484.3

(51) Int. Cl.

| | | |
|---|---|---|
| *A61Q 19/10* | (2006.01) | |
| *A61K 8/36* | (2006.01) | |
| *A61K 8/365* | (2006.01) | |
| *A61K 8/37* | (2006.01) | |
| *A61K 8/44* | (2006.01) | |
| *A61K 8/19* | (2006.01) | |
| *A61K 8/73* | (2006.01) | |
| *A61Q 5/02* | (2006.01) | |
| *A61K 8/04* | (2006.01) | |
| *A61K 8/92* | (2006.01) | |

(52) U.S. Cl.
CPC .............. *A61K 8/361* (2013.01); *A61K 8/046* (2013.01); *A61K 8/19* (2013.01); *A61K 8/365* (2013.01); *A61K 8/37* (2013.01); *A61K 8/44* (2013.01); *A61K 8/737* (2013.01); *A61K 8/922* (2013.01); *A61Q 5/02* (2013.01); *A61Q 19/10* (2013.01); *A61K 2800/596* (2013.01)

(58) Field of Classification Search
CPC .... A61Q 5/02; A61Q 19/10; A61K 2800/596; A61K 8/37; A61K 8/046; A61K 8/922; A61K 8/361; A61K 31/19; A61K 8/92; A61K 8/0216; A61K 2800/5422; A61K 8/365; A61K 8/737; A61K 8/44
USPC ......................................................... 510/121
See application file for complete search history.

(56) References Cited

U.S. PATENT DOCUMENTS

| | | | | |
|---|---|---|---|---|
| 4,292,192 A | * | 9/1981 | Hooper ..................... | A61K 8/37 510/505 |
| 6,218,348 B1 | * | 4/2001 | Aronson ................ | C11D 3/046 510/153 |
| 6,342,470 B1 | * | 1/2002 | Aronson .............. | C11D 17/006 510/141 |
| 2003/0033678 A1 | * | 2/2003 | Schulze zur Wiesche ................. | A61K 8/0216 8/405 |
| 2013/0303503 A1 | * | 11/2013 | Smith, III ............ | A61K 8/4933 514/188 |
| 2014/0378363 A1 | * | 12/2014 | Thiessies ................ | C11D 3/222 510/151 |
| 2016/0074315 A1 | * | 3/2016 | Caetano ................ | A61K 8/9789 424/59 |
| 2017/0348200 A1 | * | 12/2017 | Mathonneau .......... | A61K 8/463 |
| 2018/0092831 A1 | * | 4/2018 | Guskey .................. | A61K 8/362 |

FOREIGN PATENT DOCUMENTS

| | | |
|---|---|---|
| DE | 2736770 A1 | 2/1978 |
| DE | 102012203688 A1 | 9/2013 |
| JP | 2020083846 A | 6/2020 |

* cited by examiner

*Primary Examiner* — Eisa B Elhilo
(74) *Attorney, Agent, or Firm* — Lorenz & Kopf, LLP

(57) ABSTRACT

A cosmetic cleansing composition, which is solid at about 25° C., is disclosed. The cosmetic cleansing composition includes up to about 90% by weight, based on a total weight of the cosmetic cleansing composition, of alkali metal salts of fatty acids (soaps), from about 1 to about 40% by weight, based on a total weight of the cosmetic cleansing composition, of amino acid surfactant(s), and from about 0.05 to about 10% by weight, based on a total weight of the cosmetic cleansing composition, of citric acid ester and/or salt(s) of citric acid.

18 Claims, No Drawings

COMBAR FOR SKIN AND HAIR TREATMENT

CROSS-REFERENCE TO RELATED APPLICATION

This application claims priority to German Patent Application No. 10 2019 210 484.3, filed Jul. 16, 2020, which is incorporated herein by reference in its entirety.

TECHNICAL FIELD

The present disclosure relates to natural solid cleansing and conditioning compositions or agents for skin and especially hair, which satisfy the increased consumer demand for ecologically acceptable and natural products.

BACKGROUND

There is currently an increased consumer interest in cosmetic products that carry a natural cosmetics label and are free of critically discussed ingredients. To give the consumer the certainty of buying an ecologically sound and safe natural product, there are a number of certification companies that award appropriate seals after examining each individual case.

Among other things, the BDIH label is well known here as an identification mark for products that meet the strict requirements for genuine natural cosmetics. Currently, around 200 licensees with more than 300 brands have the BDIH label (Federal Association of Industrial and Trading Companies for Drugs, Healthcare Products, Food Supplements and Cosmetics, BDIH for short). About 40 are located in other European countries and another 40 outside Europe. In total, there are currently about 9000 products that have been declared with the BDIH seal.

In addition to the BDIH seal for controlled natural cosmetics, other seals such as the French "Ecocert" label were established. "Organic" stands for the same ingredient requirements as another one, the "NaTrue Seal". The same applies to "Made with organic ingredients". On American products there is the "USDA seal", in England additionally the label "Soil Association".

Since 2010, a further seal called "Cosmos" has been established for the natural and organic cosmetics sector. The new label is binding for all new developments in natural and organic cosmetics. It applies to all members of BDIH, Cosmebio, ICEA, Ecocert and Soil Association. They collectively represent the world's largest system for the certification of organic farming products. Since then, products of the members have been certified according to the international Cosmos standard AISBL. Several thousand raw materials and also products have already successfully passed the requirements tests during this time. All products which are registered and tested as natural or organic cosmetics after Jan. 1, 2017 will then receive Cosmos certification from the respective member organisation. For example, there is Cosmos-BDIH or Cosmos-Ecocert label.

A distinction is made between the inspection of natural cosmetics and the certification of organic products. The latter must provide evidence of additionally required proportions of ingredients from organic farming. For example, at least about 95 percent of the plant ingredients used in an organic cosmetic product must come from organic farming.

Another way to ensure a higher percentage of naturalness of raw materials in cosmetic products is the calculation according to ISO 16128. Here consumers want to buy products with a naturalness content of about 90% or more.

There is also a trend towards products that can do without plastic packaging. Low-water systems such as soaps, syndets or combars are ideal here. In order to guarantee a good performance on skin and hair with simultaneous mildness, only a few foaming surfactants in powder form are available, which also meet the Cosmos standard.

There is therefore a demand for cosmetic cleansing and conditioning products for skin and especially hair which are Cosmos-certifiable and can be sold with a significantly reduced packaging effort.

SUMMARY

The present disclosure solves the problems mentioned above. Furthermore, the present disclosure provides Cosmos-certifiable cosmetic cleansing and conditioning compositions for skin and especially hair, which have an excellent foaming behaviour and which do not leave any residues, such as lime soap deposits, on the hair and/or the skin, thus achieving an improved care performance.

The tasks underlying the present disclosure are solved by the formulations, procedures, and uses described in detail below.

A cosmetic cleansing composition that is solid at about 25° C., comprising:
  a) up to about 90% by weight, based on a total weight of the cosmetic cleansing composition, of alkali metal salts of fatty acids (soaps);
  b) from about 1 to about 40% by weight, based on a total weight of the cosmetic cleansing composition, of amino acid surfactant(s); and
  c) from about 0.05 to about 10% by weight, based on a total weight of the cosmetic cleansing composition, of citric acid ester and/or salt(s) of citric acid.

By combining specific soaps, amino acid surfactants as well as citric acid esters and/or citric acid salts, cosmos-certifiable, solid cosmetic cleansing compositions can be made available which, depending on the piece size, are also suitable for single application.

The solid cleaning compositions can be packed in an environmentally friendly way, i.e. in recyclable glass containers or in cardboard boxes.

In addition, the solid cosmetic cleansing compositions have excellent foaming properties.

For the purposes of the present disclosure, "foaming behaviour" means that the solid compositions rapidly foam up on contact with water and develop high foam quantities of a fine-bubble, creamy foam with an excellent feel, which spreads well on the skin and/or hair and rinses off well and leaves a clean, well-groomed feeling on the skin and/or hair.

A further advantage is that the application of the compositions of the present disclosure does not leave any undesirable soap residues on the skin and/or hair. In addition, it was found that the water loss sometimes occurring in standard soaps after production is significantly reduced with the compositions of the present disclosure.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The cleansing compositions of the present disclosure are solid at about 25° C. Solid substances within the meaning of the present application are three-dimensional dimensionally stable structures which are not liquid or gaseous, i.e. which retain their external shape even without a surrounding vessel. However, the term "solid" does not imply anything about density or elasticity or other physical properties, so that jellies, brawn, butter etc. can also be solid as contemplated herein as long as they are dimensionally stable at about 25° C.

The cleansing compositions of the present disclosure contain as the first ingredient one or more soap(s) in a total amount of all alkali salts of fatty acids of from about 5 to about 90% by weight. The soap(s) is/are used with particular preference within narrower quantity ranges. Here, as contemplated herein, preferred cosmetic cleansers contain from about 10 to about 89% by weight, preferably from about 20 to about 88% by weight, more preferably from about 30 to about 87% by weight, still more preferably from about 40 to about 86% by weight and in particular from about 50 to about 85% by weight of alkali metal salts of fatty acids (soaps).

Fatty acids are aliphatic carboxylic acids corresponding to the formula $R^1CO$—OH, in which $R^1CO$ is an aliphatic, linear or branched acyl radical containing 6 to 22 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid as well as their technical mixtures, which are used for the production of the following e.g. resulting from the pressure splitting of natural fats and oils. Preference is given to technical fatty acids with 12 to 18 carbon atoms, such as lauric, coconut, palm, palm kernel oleic, linoleic or tallow fatty acids, with regard to the present disclosure the use of coconut fatty acids and/or fatty acids from natural sources such as vegetable oils, for example sunflower oil, olive oil, rapeseed oil, sesame oil, wheat germ oil and/or oils or fatty acids obtained by fermentation from algae.

Particular preference is given to avoiding the use of raw materials made from palm oil or using palm oil obtained from sustainable sources according to Mass Balance.

Especially preferred cleansing compositions as contemplated herein are free from soaps made from palm oil.

Among the alkali salts, the sodium salts are particularly preferred in the context of the present disclosure due to their technical application properties. Very particularly preferred cosmetic cleansers of the present disclosure contain from about 10 to about 89% by weight, preferably from about 20 to about 88% by weight, more preferably from about 30 to about 87% by weight, even more preferably from about 40 to about 86% by weight and in particular from about 50 to about 85% by weight of sodium salts of $C_{12-18}$ fatty acids.

Particularly preferred cleansers of the present disclosure contain sodium salts of coconut fatty acids and/or of fatty acids from natural sources such as vegetable oils, for example sunflower oil, olive oil, rapeseed oil, sesame oil, wheat germ oil and/or oils or fatty acids obtained by fermentation from algae.

Especially preferred are the soaps known under the INCI designations Sodium Cocoate and/or Sodium Sunflowerseedate.

The cleansers as contemplated herein contain from about 2 to about 50% by weight of amino acid surfactant(s) as the second ingredient.

Washing-active (anionic) amino acid surfactants are particularly mild surfactants that are available from natural sources and are biodegradable. They counteract the loss of moisture from the skin during cleansing and have an extremely low to no skin irritation potential. As a result, they are particularly suitable for use in the compositions as contemplated herein.

With particular preference, the cosmetic cleansers as contemplated herein contain from about 3 to about 40% by weight, preferably from about 4 to about 35% by weight, more preferably from about 5 to about 30% by weight, even more preferably from about 6 to about 25% by weight and in particular from about 7.5 to about 15% by weight of amino acid surfactants corresponding to formula (Ia) and/or (Ib)

in which
$R^1CO$ is a linear or branched acyl radical having 6 to 22 carbon atoms and 0 and/or 1, 2 or 3 double bonds,
$R^2$ is H or for $C_1$-$C_4$ alkyl group,
$R^3$, $R^4$ independent of one another represent —H, a $C_1$-$C_4$ alkyl group or —$(CH_2)_p$—COOX,
n, p is 1, 2 or 3, and
X in each case represents hydrogen, an alkali and/or alkaline earth metal, ammonium, alkylammonium, alkanolammonium or glucammonium.

Alkali metal and/or ammonium salts of acyltaurates, acyl glutamates, acylglycinates, acylalaninates, acylsarcosinates and/or acylaspartates are particularly preferred, and particularly preferred are sodium, potassium or ammonium salts of the aforementioned amino acids, where the term means lauryol, cocoyl and/or myristoyl.

Alkali metal and/or ammonium salts of acyltaurates, acyl glutamates and/or acylglycinates, in which lauryol, cocoyl and/or myristoyl are particularly preferred.

In particular preferred cleansers of the present disclosure contain, based on their weight, from about 1.5 to about 35% by weight, preferably from about 2.0 to about 30% by weight, more preferably from about 2.5 to about 25% by weight, still more preferably from about 3.0 to about 20% by weight and in particular from about 3.5 to about 15% by weight of acyl glutamates corresponding to formula (Ia)

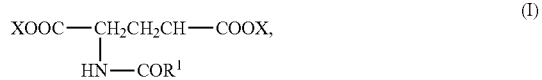

in which $R^1CO$ is a linear or branched acyl radical containing 6 to 22 carbon atoms and 0 and/or 1, 2 or 3 double bonds and X is hydrogen, an alkali metal and/or alkaline earth metal, ammonium, alkylammonium, alkanolammonium or glucammonium.

Within this version, acyl glutamates in which X represents Na and $R^1CO$ represents an acyl radical derived from coconut oil (INCI: Sodium Cocoyl Glutamate) is particularly preferred.

The use of acyl amino acid surfactants, in particular acyl glutamates, in the compositions as contemplated herein leads to skin mild compositions which foam well, form a fine pored, stable foam and leave a pleasant skin feeling.

The cleansing compositions as contemplated herein contain from about 0.05 to about 10% by weight of citric acid ester and/or citric acid salt(s) (based on their weight) as a third ingredient to further optimize the foaming behaviour.

Suitable citric acid esters within the meaning of the present disclosure preferably correspond to the following formula (II)

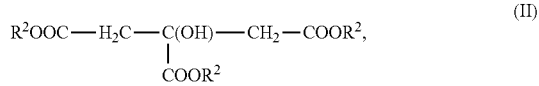

in which $R^2$ in each case represents a saturated or unsaturated, branched or unbranched $C_1$-$C_{10}$ alkyl radical.

Preferred cleansers as contemplated herein contain, based on their weight, from about 0.075 to about 9% by weight, preferably from about 0.1 to about 8% by weight, more preferably from about 0.15 to about 7% by weight, still more preferably from about 0.2 to about 6% by weight and more preferably from about 0.25 to about 5% by weight of citric acid esters corresponding to formula (II) above, in which $R^2$ in each case represents a saturated or unsaturated, branched or unbranched $C_1$-$C_{10}$ alkyl radical.

Especially preferred are cleansing compositions as contemplated herein which contain triethyl citrate, tributyl citrate and/or trioctyl citrate in the aforementioned quantities.

Suitable citric acid salts within the meaning of the present disclosure preferably correspond to the following formula (III)

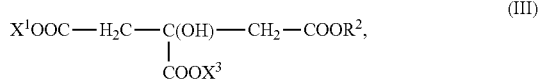

in which $X^1$, $X^2$, $X^3$ are each —H, an alkali metal or an alkaline earth metal cation, at least one of $X^1$, $X^2$, $X^3$ not being —H.

Further preferred cleansers as contemplated herein contain, based on their weight, from about 0.075 to about 9% by weight, preferably from about 0.1 to about 8% by weight, more preferably from about 0.15 to about 7% by weight, still more preferably from about 0.2 to about 6% by weight and in particular from about 0.25 to about 5% by weight of citric acid salt(s) of the above-mentioned formula (III), particularly preferably monocitrate salt(s) and/or tricitrate salt(s) and very particularly preferably sodium, potassium and/or magnesium mono- and/or tricitrate salts.

It was found that citric acid esters improve the overall foaming behaviour of the compositions of the present disclosure. A further advantage is that even the use of hard water during cleaning with the compositions of the present disclosure has no negative effect on the foam development and the foam quality of the compositions or agents, so that uniform results can be achieved regardless of whether one is in a region with hard or soft water. Particularly satisfactory results were obtained when triethyl citrate was used.

In particular, the cleansers as contemplated herein therefore preferably contain triethyl citrate in the aforementioned quantities.

In addition to the soap(s) and acyl glutamate(s), the cleansers as contemplated herein may contain other surfactants. In view of the above-mentioned problem and the skin-friendliness of the cleansers or products, it has proved to be advantageous to use only surfactants from certain substance groups. Cosmetic cleansers as contemplated herein which exclusively contain surfactant (s) from the groups of alkyl oligo- and polysaccharides betaines have proven to be particularly advantageous with regard to consumer acceptance,
skin friendliness and the
application properties.

It is particularly preferred if the cosmetic cleansers as contemplated herein contain, based on their weight, less than about 1% by weight, preferably less than about 0.75% by weight, more preferably less than about 0.5% by weight, still more preferably less than about 0.25% by weight and in particular less than about 0.1% by weight of sulphate-containing surfactant(s), extremely preferred cleansers being completely free from sulphate-containing surfactants.

The other preferred surfactants are described below.

Alkyl and alkenyl oligoglycosides are known non-ionic surfactants which can be described by the formula $R^1O$-$[G]_p$, in which $R^1$ is an alkyl and/or alkenyl radical having 4 to 22 carbon atoms, G is a sugar radical having 5 or 6 carbon atoms and p is a number from about 1 to about 10. They can be obtained by the relevant methods of preparative organic chemistry.

The alkyl and/or alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula indicates the degree of oligomerisation (DP), i.e. the distribution of monoglycosides and oligoglycosides and is a number between about 1 and about 10. While p in a given compound must always be an integer and can assume the values p=1 to 6, the value p for a particular alkyl oligo-glycoside is an analytically determined arithmetical quantity which usually represents a fractional number. Preferably alkyl and/or alkenyl oligoglycosides with an average degree of oligomerization p of from about 1.1 to about 3.0 is used. From an application technology point of view, those alkyls and/or alkenyl oligoglycosides are preferred whose degree of oligomerization is less than about 1.7 and in particular lies between about 1.2 and about 1.4. The alkyl or alkenyl radical $R^1$ can be derived from primary alcohols containing 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or in the course of the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than about 6% by weight of $C_{12}$ alcohol, and alkyl oligoglucosides based on technical $C_{9/11}$ oxoalcohols (DP=1 to 3). The alkyl or alkenyl radical R1 can also be derived from primary alcohols having 12 to 22, preferably 12 to 14 carbon atoms. Typical examples are lauryl alcohol, my-ristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Preferred cleansers as contemplated herein contain from about 0.1 to about 10% by weight, preferably from about 0.25 to about 7.5% by weight, more preferably from about 0.5 to about 5% by weight, still more preferably from about 0.75 to about 2.5% by weight and in particular from about 1 to about 2% by weight of surfactant(s) from the group of alkyl oligo- and polysaccharides.

Betaines are known surfactants which are predominantly produced by carboxyalkylation, preferably carb-oxymethylation of aminic compounds. The starting materials are preferably condensed with halocarboxylic acids or their salts, in particular with sodium chloroacetate, whereby one mole of salt is formed per mole of betaine. Furthermore, the addition of unsaturated carboxylic acids, such as acrylic acid, is also possible. Examples of suitable betaines are the carboxyalkylation products of secondary and in particular tertiary amines which can be described by the formula

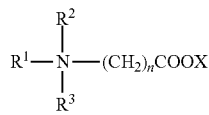

in which $R^1$ is alkyl and/or alkenyl radicals having 6 to 22 carbon atoms, $R^2$ is hydrogen or alkyl radicals having 1 to 4 carbon atoms, $R^3$ is alkyl radicals having 1 to 4 carbon atoms, n is numbers from 1 to 6 and X is an alkali and/or alkaline earth metal or ammonium. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$ cocoalkyldimethylamine, myristyldimethylamine, cetyldimethylamine, stearyldimethylamine, stearylethylmethylamine, oleyldimethylamine, $C_{16/18}$ tallow alkyldimethylamine and their technical mixtures.

Furthermore, carboxyalkylation products of amidoamines can also be considered, which are represented by the formula

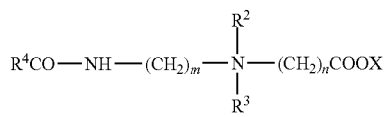

in which $R^4CO$ is an aliphatic acyl radical having 6 to 22 carbon atoms and 0 or 1 to 3 double bonds, m is numbers from 1 to 3 and $R^2$, $R^3$, n and X have the meanings given above. Typical examples are reaction products of fatty acids with 6 to 22 carbon atoms, namely caproic acid, caprylic acid, capric acid, lauric acid, myristic acid, palmitic acid, palmoleic acid, stearic acid, isostearic acid, oleic acid, elaidic acid, petroselinic acid, linoleic acid, Linolenic acid, elaeostearic acid, arachidic acid, gadoleic acid, behenic acid and erucic acid, and technical mixtures thereof, with N,N-dimethylaminoethylamine, N,N-dimethylaminopropylamine, N,N-diethylaminoethylamine and N,N-diethylaminopropylamine which are condensed with sodium chloroacetate. Preferred is the use of a condensation product of $C_{8/18}$ coconut fatty acid N,N-dime-ethylaminopropylamide with sodium chloroacetate.

Furthermore, imidazolines which can be described by the formula in which $R^5$ is an alkyl radical having 5 to 21 carbon atoms,

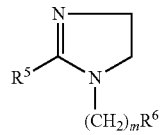

$R^6$ is a hydroxyl group, an $OCOR^5$ or $NHCOR^5$ radical and m is 2 or 3 are also considered as suitable starting materials for the betaines to be used as contemplated herein. These substances are also known substances that can be obtained, for example, by cyclizing condensation of 1 or 2 moles of fatty acid with polyvalent amines, such as aminoethylethanolamine (AEEA) or diethylenetriamine. The corresponding carboxyalkylation products are mixtures of different open-chain betaines. Typical examples are condensation products of the above-mentioned fatty acids with AEEA, preferably imidazolines based on lauric acid or again $C_{12/14}$ coconut fatty acid, which are subsequently betaine treated with sodium chloroacetate.

Preferred cleansing compositions as contemplated herein contain from about 0.5 to about 20% by weight, preferably from about 1 to about 15% by weight, more preferably from about 1.5 to about 12% by weight, still more preferably from about 2 to about 10% by weight and in particular from about 2.5 to about 8% by weight of at least one amphoteric and/or zwitterionic surfactant.

Particularly preferred cleansers as contemplated herein contain from about 0.5 to about 20% by weight, preferably from about 1 to about 15% by weight, more preferably from about 1.5 to about 12% by weight, still more preferably from about 2 to about 10% by weight and in particular from about 2.5 to about 8% by weight of amphoteric and/or zwitterionic surfactant known at least under the INCI designation cocamidopropyl betaine.

In addition to the soap(s), amino acid surfactant(s) and citric acid ester(s) and/or citric acid salt(s), the cleansers as contemplated herein may contain at least one natural, not chemically modified polymer. Such substances, also known as biopolymers, come in particular from the group of polysaccharides. The use of cellulose, starch, guar gum or xanthan is particularly preferred.

"Not chemically modified" means that the natural polymer has not been subjected to chemical reactions to affect its properties. Physical modifications, on the other hand, are possible and common e.g. for starch and xanthan gum (pregelatinized, cooked, cold swelling or instantaneous starches, heat treated xanthan gum). Physically modified starches are on an equal footing with native starches because they are only thermally treated, i.e. cooked.

Irrespective of whether only one or more natural polymer(s) is/are used, cosmetic cleansers as contemplated herein are preferred which contain from about 0.1 to about 10% by weight, preferably from about 0.25 to about 9% by weight, more preferably from about 0.5 to about 8% by weight, still more preferably from about 0.75 to about 7% by weight and in particular from about 1 to about 6% by weight of natural, non-modified polymer(s).

It is particularly advantageous that the compositions as contemplated herein contain from about 0.1 to about 5% by weight of guaran (INCI designation Guar gum).

Guaran, also called Guar gum, is a vegetable gum. The chemical compound from the group of polysaccharides is the main component of Guar gum (or guar flour for short). Guaran includes D-mannopyranose units, which are linked together in chains via β-glycosidic bonds. Furthermore, every second mannopyranose unit carries α-D-galactopyranosyl residues via a-bond.

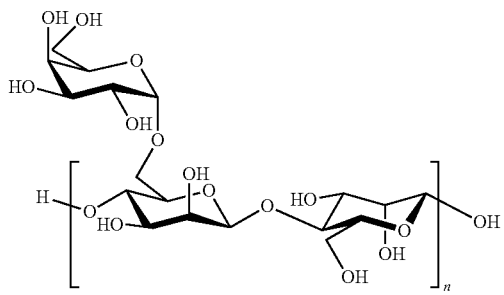

Preferably the Guar Gum is used in smaller quantities. Here, preferred cleansing compositions as contemplated herein contain from about 0.2 to about 4% by weight, preferably from about 0.3 to about 3.5% by weight, more preferably from about 0.4 to about 3% by weight, even more preferably from about 0.45 to about 2.5% by weight, and in particular from about 0.5 to about 2% by weight of guaran.

The compositions as contemplated herein may preferably contain from about 0.1 to about 5 wt. % Xanthan gum (INCI designation Xanthan gum). Xanthan gum is a natural, renewable raw material and is excreted as an anionic polysaccharide by the bacterium *Xanthomonas campestris*.

The preferred molecular weight of the Xanthan gum used is $2 \cdot 10^6$ to $20 \cdot 10^6$ g/mol.

As molecular building blocks, xanthan gum contains D-glucose, D-mannose, D-glucuronic acid, acetate and pyruvate in any molar ratio of from about 28 to about 30 to about 20 to about 17 to about 5.1 to about 6.3. The polymer backbone of xanthan gum is formed from a cellulose chain of β-1.4-bound glucose units. Xanthan contains structural units of the following formula Heat-treated Xanthan gum may also be used in the cosmetic cleansing compositions as contemplated herein.

In a preferred form, the cleanser of the present disclosure contains as Xanthan gum
heat-treated Xanthan gum, or
a mixture of Xanthan gum and heat-treated Xanthan gum.

When using a mixture of Xanthan gum and heat-treated Xanthan gum, it has been found to be particularly effective to use the Xanthan gum and the heat-treated Xanthan gum in a weight ratio range from about 2:1 to about 1:20, in particular from about 1:2 to about 1:10.

As contemplated herein, heat-treated Xanthan gum is Xanthan gum that is exposed to heat of at least about 40° C. The resulting heat-treated Xanthan gum has improved dispersibility and can be dispersed in water faster than Xanthan gum that has not been subjected to heat treatment. The preferably suitable heat-treated Xanthan gum has a viscosity of at least about 25000 to about 40000 mPa·s in about 1% by weight aqueous solution (Brookfield DV-I viscometer, spindle #6 at 23° C. and 10 rpm). Preferably used heat-treated Xanthan gums provide a pH of about 4.0 to about 6.0 at about 23° C. when prepared in about 1% by weight aqueous solution.

The heat-treated Xanthan gum preferred by the present disclosure was obtained by tempering Xanthan gum at a temperature of at least about 60° C., in particular at least about 100° C. Tempering can be achieved by a variety of known methods, such as oven, fluidized bed, infrared or microwave heat treatment. Within the framework of the above-mentioned heat treatments, it is again preferable for the Xanthan gum to have a water content of less than about 25% by weight, in particular less than about 8% by weight, very preferably less than about 3% by weight, before the heat treatment. It is further preferred, as contemplated herein, to use in the composition of the present disclosure such heat-treated Xanthan gum obtained by heat-treating Xanthan gum with a water content of less than about 25% by weight at a temperature of at least about 60° C. (in particular of at least about 100° C.) for at least about 30 minutes. As contemplated herein, it is particularly preferred to use in the composition of the present disclosure such heat-treated Xanthan gum in which Xanthan gum with a water content of less than about 8% by weight is heat-treated at a temperature

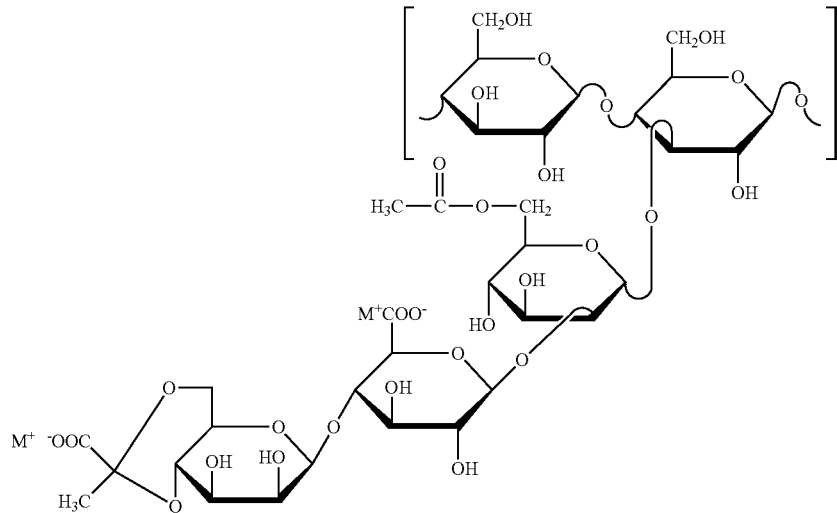

$M^+$ = Na, K, 1/2 Ca of at least about 60° C. (in particular of at least about 100° C.) for at least about 30 minutes. The preferred duration of the above-mentioned heat treatments of the Xanthan gum—especially with the said water content—at a temperature of at least about 60° C. (especially of at least about 100° C.) is at least about 1 hour. The particularly preferred duration of the above-mentioned heat treatments of the Xanthan gum, especially with the preferred water content, at a temperature of at least about 60° C. (especially of at least about 100° C.) shall be at least about 2.5 hours.

Preferably, Xanthan gum, regardless of whether it is heat-treated or non-heat-treated or a mixture of both, is used in narrower quantity ranges. Here, preferred cleansing compositions as contemplated herein contain from about 0.1 to about 10% by weight, preferably from about 0.15 to about 8% by weight, more preferably from about 0.2 to about 6% by weight, still more preferably from about 0.25 to about 5% by weight and in particular from about 0.3 to about 4% by weight of Xanthane.

As already mentioned earlier, the cleansing compositions as contemplated herein contain relatively little water. This saves both resources (water) and packaging material.

With particular preference, the solid cleansers as contemplated herein contain less than about 25% by weight, preferably less than about 22% by weight, more preferably less than about 20% by weight, still more preferably less than about 18% by weight and in particular less than about 15% by weight of water.

With special preference, the compositions of the present disclosure may contain further components, whereby natural skin caring, and refatting substances are particularly suitable. The use of native oils is particularly preferred, so that cosmetic cleansers containing from about 0.1 to about 10% by weight, preferably from about 0.25 to about 9% by weight, more preferably from about 0.5 to about 8% by weight, still more preferably from about 0.75 to about 7% by weight and more preferably from about 1 to about 6% by weight of natural oil(s) are preferred.

With particular preference, the compositions of the present disclosure contain one or more of the following oils in a total quantity of oil as defined above: Açaí oil, algae oil, argan oil (from the fruits of the argan tree), avocado oil (from the pulp of the avocado of the avocado tree), babaçu oil, cotton seed oil (from the seeds of the cotton plant), borage oil or borage seed oil (from the seeds of the borage plant), Cupuacu butter, cashew shell oil, Safflower oil (also called "safflower oil", from the seeds of safflower or Carthamus), peanut oil (from the fruit of the peanut plant), hazelnut oil (from the hazelnuts of the hazelnut bush), hemp oil (from the seeds of edible hemp), jatropha oil (from the seeds of jatropha curcas), jojoba oil (actually a liquid wax; from the seeds of the jojoba bush), *camellia* oil (from the seeds of *Camellia oleifera, Camellia sinensis* or *Camellia japonica*, cocoa butter, coconut oil (from the seed flesh of the coconut, the fruit of the coconut palm), pumpkin seed oil (also known as kernel oil; from the seeds of the Styrian oil pumpkin), linseed oil (from the ripe linseeds of the flax), gold of pleasure oil (from the seeds of the gold of pleasure, family of the cruciferous plants), macadamia oil (from the nuts of the macadamia tree), corn germ oil (from the germ of corn), almond oil (from the almonds of the almond tree), mango butter (from *Mangifera indica*), apricot kernel oil or Apricot kernel oil (from the apricot kernel—the almond of the apricot stone—of the apricot or apricot), poppy seed oil (from the seeds of the poppy), evening primrose oil, olive oil (from the pulp and kernel of the olive, the fruit of the olive tree, palm oil (from the pulp of the palm fruit, the fruit of the oil palm), palm kernel oil (from the kernels of the palm fruit, the fruit of the oil palm), Papaya oil, pistachio oil, pecan oil, perilla oil from the seeds of the perilla plant (shiso, sesame leaf), rapeseed oil (from the seed of rapeseed, family of cruciferous plants), rice oil, castor oil (from the seed of the miracle tree), sea buckthorn oil (from the pulp of the sea buckthorn berry, the fruit of the sea buckthorn bush), sea buckthorn seed oil (from the seeds of the sea buckthorn berry, the fruit of the sea buckthorn bush), mustard oil (from the seeds of the black mustard), black cumin oil (from the seeds of the fruit capsule of the black cumin plant), sesame oil (from the seeds of the sesame plant), Shea butter (from the seeds of the Shea nut tree), soy bean oil (from the beans of the soy bean), sunflower oil (from the seeds of the sunflower), tung oil, walnut oil (from the seeds of the walnut tree nuts), watermelon seed oil, grape seed oil (from the seeds of the fruits (grape) of the vine plant or grapevine), wheat germ oil (from the seeds of the wheat), cedar oil (from the wood of the Lebanon cedar).

In a preferred embodiment, the cleansing compositions as contemplated herein contain, based on their weight, from about 0.1 to about 10% by weight, preferably from about 0.25 to about 9% by weight, more preferably from about 0.5 to about 8% by weight, still more preferably from about 0.75 to about 7% by weight and in particular from about 1 to about 6% by weight of coconut oil, sunflower oil, olive oil, rapeseed oil, jojoba oil, almond oil, avocado oil, shea butter, cocoa butter and/or castor oil.

The cleansers as contemplated herein may contain further ingredients, whereby in view of the task, attention should be paid to the use of COSMOS-certified raw materials.

A second object of the present disclosure is the use of citric acid esters of formula (II) and/or citric acid salts of formula (III)

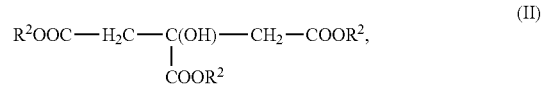

(II)

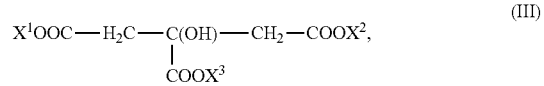

(III)

located in the
R² each represents a $C_1$-$C_{10}$ alkyl radical, or
$X^1$, $X^2$, $X^3$ are each —H, an alkali metal or an alkaline earth metal cation, at least one of $X^1$, $X^2$, $X^3$ not being —H,
for improving the foaming behaviour of solid cosmetic cleansers, in particular combars containing soaps and amino acid surfactants.

The use of triethyl citrate is particularly suitable.

A third subject-matter of the present disclosure is the use of the solid cleansing composition as contemplated herein for cleaning and care of the human body, including the hair.

A fourth subject-matter of the present disclosure is a process for cleaning and caring for the human body, including the hair, in which a solid cleansing composition
  of the present disclosure mixed with water until foam is formed and then spread over the part of the body to be cleaned, or is distributed directly on the wet part of the body
  is distributed directly on the wet part of the body to be cleaned by friction, thus forming a foam, and the foam is rinsed with water after an exposure time of one second to five minutes.

Examples

The following composition can be produced as an example (all data in weight %):

|  | 01 | 02 | 03 | 04 | 05 | 06 | 07 | 08 | 09 |
|---|---|---|---|---|---|---|---|---|---|
| Soaplex Hoso Organic ®[1] | 86.00 | 91.00 | 87.50 |  |  | 85.30 | 87.50 | 86.00 |  |
| BV 421—100% Olive 100 ®[2] (Olive)—ivory |  |  |  | 90.5 | 87.5 |  |  |  | 40.3 |
| BV 842—100% Coconut 100 (CNO) ®[3] |  |  |  |  |  |  |  |  | 40 |
| Sodium Cocoyl Glutamate | 5.00 |  | 10 | 5 | 3 | 8 |  | 5.00 | 10 |
| Sodium cocoyl Glycinate |  | 3 |  |  | 3 |  | 2 |  |  |
| Triethylcitrate | 0.50 | 1 |  |  |  | 1 |  | 0.50 | 2 |
| Magnesium Citrate |  | 0.5 |  | 0.5 |  |  | 2 |  |  |
| Tego Betaine CK D ®[4] | 4.50 | 1 | 1 | 1 | 2 | 3 | 2 | 4.50 | 5 |
| APG |  | 1 |  | 1 |  | 1 | 2 |  | 1 |
| Sodium Lauroyl Lactylate |  |  |  |  | 2 |  | 2 |  |  |
| Xanthan | 1.00 |  |  |  |  | 1 |  | 1.00 |  |
| Guar Gum |  | 1 |  |  | 0.5 |  | 0.5 |  |  |
| Biosaccharid Gum 1 |  |  |  | 0.2 |  |  |  |  | 0.2 |
| Avocado Oil |  |  |  |  |  | 0.5 |  |  |  |
| Cocos Oil | 2.00 | 0.5 |  |  | 1 |  |  | 2.00 |  |
| Abyssinian Oil |  |  | 0.5 |  |  |  | 1 |  | 0.5 |
| Castor Oil |  |  |  | 0.5 |  | 0.2 |  |  |  |
| Perfume (Fragrance) | 1.00 | 1.00 | 1.00 | 1.00 | 1.00 | 1.00 | 1.00 | 1.00 | 1.00 |

[1]INCI designation: Sodium Sunflowerseedate, sodium cocoate, Aqua; available from Sandralex
[2]available from Cremer Oleo Division
[3]available from Cremer Oleo Division
[4]INCI designation: Cocamidopropylbetaine; available from Evonik

What is claimed is:

1. A cosmetic cleansing composition that is solid at about 25° C., comprising:
   a) up to about 90% by weight, based on a total weight of the cosmetic cleansing composition, of alkali metal salts of fatty acids (soaps);
   b) from about 1 to about 40% by weight, based on a total weight of the cosmetic cleansing composition, of amino acid surfactant(s); and
   c) from about 0.05 to about 10% by weight, based on a total weight of the cosmetic cleansing composition, of citric acid ester and/or salt(s) of citric acid;
   wherein the cosmetic cleansing composition is free from sulphate-containing surfactants and wherein the cosmetic cleansing composition is further free from soaps made from palm oil.

2. The cosmetic cleansing composition according to claim 1, wherein the cosmetic cleansing composition comprises, based on a total weight of the cosmetic cleansing composition, from about 10 to about 89% by weight of the alkali metal salts of fatty acids (soaps).

3. The cosmetic cleansing composition according to claim 2, wherein the alkali metal salts of fatty acids (soaps) are sodium salts of $C_{12-18}$ fatty acids.

4. The cosmetic cleansing composition according to claim 1, wherein the cosmetic cleansing composition comprises from about 1.5 to about 35% by weight, based on a total weight of the cosmetic cleansing composition, of the amino acid surfactant(s), and wherein the amino acid surfactant(s) is selected from taurate, glutamate, glycinate, alaninate, sarcosinate, and/or aspartate surfactants.

5. The cosmetic cleansing composition according to claim 1, wherein the amino acid surfactant(s) is an acyl glutamate corresponding to formula (I)

$$\text{XOOC}-\text{CH}_2\text{CH}_2\text{CH}-\text{COOX}, \atop | \atop \text{HN}-\text{COR}^1 \qquad (I)$$

wherein $R^1CO$ is a linear or branched acyl radical comprising 6 to 22 carbon atoms and 0 and/or 1, 2 or 3 double bonds and X is hydrogen, an alkali metal and/or alkaline earth metal, ammonium, alkylammonium, alkanolammonium or glucammonium, and wherein the cosmetic cleansing composition comprises, based on a total weight of the cosmetic cleansing composition, from about 1.5 to about 35% by weight of the acyl glutamate.

6. The cosmetic cleansing composition according to claim 1, wherein the cosmetic cleansing composition comprises, based on a total weight of the cosmetic cleansing composition, from about 0.075 to about 9% by weight of the citric acid esters corresponding to formula (II)

$$\text{R}^2\text{OOC}-\text{H}_2\text{C}-\text{C(OH)}-\text{CH}_2-\text{COOR}^2, \atop | \atop \text{COOR}^2 \qquad (II)$$

wherein each $R^2$ is a $C_1$-$C_{10}$ alkyl radical.

7. The cosmetic cleansing composition according to claim 6, wherein the citric acid esters is selected from triethyl citrate, tributyl citrate, and/or trioctyl citrate.

8. The cosmetic cleansing composition according to claim 1, wherein the cosmetic cleansing composition comprises, based on a total weight of the cosmetic cleansing composition, from about 0.075 to about 9% by weight of the citric acid salt(s) corresponding to formula (III)

$$\text{X}^1\text{OOC}-\text{H}_2\text{C}-\text{C(OH)}-\text{CH}_2-\text{COOX}^2, \atop | \atop \text{COOX}^3 \qquad (III)$$

wherein $X^1$, $X^2$, $X^3$ are each —H, an alkali metal, or an alkaline earth metal cation, and wherein at least one of $X^1$, $X^2$, $X^3$ not being —H.

9. The cosmetic cleansing composition according to claim 8, wherein the citric acid salt(s) comprises monocitrate salt(s) and/or tricitrate salt(s).

10. The cosmetic cleansing composition according to claim 1, wherein the cosmetic detergent composition comprises, based on a total weight of the cosmetic cleansing composition, from about 0.5 to about 20% by weight of at least one amphoteric and/or zwitterionic surfactant.

11. The cosmetic cleansing composition according to claim 1, further comprising, based on a total weight of the cosmetic cleansing composition, from about 0.1 to about 10% by weight of natural, unmodified polymer(s).

12. The cosmetic cleansing composition according to claim 11, wherein the natural, unmodified polymer(s) is xanthane.

13. The cosmetic cleansing composition according to claim 1, comprising less than about 25% by weight, based on a total weight of the cosmetic cleansing composition, of water.

14. The cosmetic detergent composition according to claim 1, further comprising, based on a total weight of the cosmetic cleansing composition, from about 0.1 to about 10% by weight natural oil(s).

15. The cosmetic cleansing composition according to claim 14, wherein the natural oil(s) is selected from coconut oil, sunflower oil, olive oil, rapeseed oil, jojoba oil, almond oil, avocado oil, shea butter, cocoa butter, and/or castor oil.

16. A method for the cleansing and care of the human body, including the hair, comprising the steps of:
   mixing the cosmetic cleansing composition of claim 1 with water to form a foam;
   spreading the cosmetic cleansing composition over a part of the body to be cleaned; and then
   rinsing the foam with water after an exposure time of from about 1 second to about 5 minutes.

17. A method for the cleansing and care of the human body, including the hair, comprising the steps of:
   distributing the cosmetic cleansing composition of claim 1 directly onto a wet part of the body to be cleaned by friction to form a foam; and then
   rinsing the foam with water after an exposure time of from about 1 second to about 5 minutes.

18. A cosmetic cleansing composition that is solid at about 25° C., comprising:
   a) from about 40 to about 90% by weight, based on a total weight of the cosmetic cleansing composition, of sodium salts of $C_{12-18}$ fatty acids;
   b) from about 3 to about 10% by weight, based on a total weight of the cosmetic cleansing composition, of an acyl glutamate corresponding to formula (I)

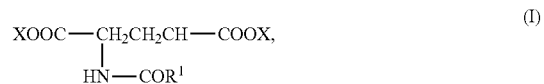

wherein $R^1CO$ is a linear or branched acyl radical comprising 6 to 22 carbon atoms and 0 and/or 1, 2 or 3 double bonds and X is hydrogen, an alkali metal and/or alkaline earth metal, ammonium, alkylammonium, alkanolammonium or glucammonium; and
   c) from about 0.25 to about 5% by weight, based on a total weight of the cosmetic cleansing composition, of tri-ethyl citrate, a monocitrate salt, and/or a tricitrate salt;
   wherein the cosmetic cleansing composition is free from a sulphate-containing surfactant and wherein the cosmetic cleansing composition is further free from soaps made from palm oil.

* * * * *

UNITED STATES PATENT AND TRADEMARK OFFICE
CERTIFICATE OF CORRECTION

PATENT NO. : 11,554,085 B2
APPLICATION NO. : 16/928704
DATED : January 17, 2023
INVENTOR(S) : Heike Schelges and Elvira Scholz It is certified that error appears in the above-identified patent and that said Letters Patent is hereby corrected as shown below:

In the Specification

Column 5, Line 39 change "$COOR^2$" to --$COOX^2$--.
Column 7, Line 2 change "$C_{12/14}$" to --C12/14--.

Signed and Sealed this
Twenty-seventh Day of February, 2024

Katherine Kelly Vidal
Director of the United States Patent and Trademark Office